United States Patent [19]

Ono et al.

[11] 4,388,469
[45] Jun. 14, 1983

[54] DIPHENYLALKANOETHER AND DIPHENYLALKANONE OXIMEETHER DERIVATIVES

[75] Inventors: Keiichi Ono, Osaka; Hajime Kawakami, Takarazuka; Junki Katsube, Toyonaka, all of Japan

[73] Assignee: Sumitomo Chemical Company, Limited, Osaka, Japan

[21] Appl. No.: 136,565

[22] Filed: Apr. 2, 1980

[30] Foreign Application Priority Data

Apr. 2, 1979 [JP] Japan ................................ 54-40032
Aug. 13, 1979 [JP] Japan ............................... 54-103340

[51] Int. Cl.$^3$ .................... C07D 333/04; C07C 87/28; C07D 307/34; A61K 31/38; A61K 31/34; A61K 31/135

[52] U.S. Cl. ...................................... 549/59; 424/275; 424/285; 549/60; 424/330; 549/61; 549/65; 549/68; 549/69; 549/75; 549/472; 549/473; 549/474; 549/476; 549/478; 549/479; 549/480; 549/481; 549/487; 549/491; 549/496; 546/261; 546/264; 546/265; 546/283; 546/284; 546/286; 546/294; 546/300; 546/312; 546/334; 260/465 E; 564/220; 564/256; 564/257; 564/346

[58] Field of Search ......... 260/566 AE, 570 R, 347.2, 260/347.7, 465 E; 546/261, 264, 266, 283, 284, 286, 287, 288, 289, 290, 291, 294, 296, 297, 300, 312, 329; 549/60, 61, 63, 65, 68, 75, 59, 62, 69, 472, 473, 474, 475, 476, 477, 478, 479, 480, 481, 487, 488, 491, 496; 564/346, 220; 424/263, 275, 285, 330

[56] References Cited

U.S. PATENT DOCUMENTS

| | | | |
|---|---|---|---|
| 3,347,858 | 10/1967 | Szarvasi et al. | 260/347.7 |
| 3,565,955 | 2/1971 | Ehrhart et al. | 260/570 R |
| 3,814,750 | 6/1974 | Cross et al. | 549/75 |
| 4,049,825 | 9/1977 | Gootjes | 424/330 |
| 4,192,818 | 3/1980 | van Dijk et al. | 260/566 AE |

FOREIGN PATENT DOCUMENTS

| | | | |
|---|---|---|---|
| 196386 | 3/1958 | Austria | 564/346 |
| 505848 | 9/1954 | Canada | 546/284 |

OTHER PUBLICATIONS

Sperber, Nathan et al., *J. Am. Chem. Soc.*, vol. 71 (1949) pp. 887-890.
Conant, James Bryant, "The Chemistry of Organic Compounds" (1947) MacMillan Co. Publ., at p. 264.
*J. Pharmacol. Exptl. Therap.*, vol. 112, 318-325 (1954).
*J. Pharm. Sci.*, vol. 54 (1965) p. 1373.
Farmaco (Pavia), Ed. Sci., vol. 19 (1964) pp. 688-702.

*Primary Examiner*—Natalie Trousof
*Assistant Examiner*—L. Hendriksen
*Attorney, Agent, or Firm*—Birch, Stewart, Kolasch and Birch

[57] ABSTRACT

Diphenylalkanoether and diphenylalkanone oxime-ether derivatives of the formula:

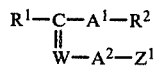

wherein $R^1$ and $R^2$ are each independently an aryl group optionally substituted with 1 to 3 substituents selected from the group consisting of halogen, $C_1$–$C_4$ alkyl, $C_1$–$C_4$ alkoxy, nitro, cyano, di($C_1$–$C_4$)alkylamino, amino, benzyloxy, hydroxyl, $C_1$–$C_4$ alkylthio, $C_1$–$C_4$ alkylsulfinyl, $C_1$–$C_4$ alkylsulfonyl, $C_1$–$C_4$ alkanoylamino, $C_1$–$C_4$ alkylamino and N-($C_1$–$C_4$)alkyl-N-($C_1$–$C_4$)alkanoylamino, $Z^1$ is a group of the formula:

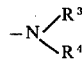

(wherein $R^3$ and $R^4$ are each independently a hydrogen atom, a $C_1$–$C_4$ alkyl group or an ar($C_1$–$C_4$)alkyl group or, when taken together with the adjacent nitrogen atom to which they are attached, represent a nitrogen-containing 5 to 7-membered saturated heterocyclic group optionally having an oxygen atom or an additional nitrogen atom as the hetero atom in addition to the said nitrogen atom and, in case of having the additional nitrogen atom, bearing a hydrogen atom, a $C_1$–$C_4$ alkyl group, an ar($C_1$–$C_4$)alkyl group or a phenyl group thereon),

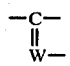

is a group of the formula:

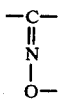

or the formula:

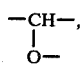

$A^1$ is a $C_2$–$C_6$ alkylene group and $A^2$ is a $C_2$–$C_4$ alkylene group, and non-toxic, pharmaceutically acceptable acid addition salts thereof, which have cerebral vasodilating activity and antihypoxic activity.

15 Claims, No Drawings

DIPHENYLALKANOETHER AND DIPHENYLALKANONE OXIMEETHER DERIVATIVES

This invention relates to diphenylalkanoether and diphenylalkanone oximeether derivatives having cerebral vasodilating activity, antihypoxic activity and the like, and to preparation and use thereof.

The said diphenylalkanoether and diphenylalkanone oximeether derivatives are represented by the formula:

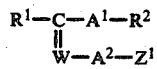         (I)

wherein $R^1$ and $R^2$ are each independently an aryl group optionally substituted with 1 to 3 substituents selected from the group consisting of halogen, $C_1$–$C_4$ alkyl, $C_1$–$C_4$ alkoxy, nitro, cyano, di($C_1$–$C_4$)alkylamino, amino, benzyloxy, hydroxyl, $C_1$–$C_4$ alkylthio, $C_1$–$C_4$ alkylsulfinyl, $C_1$–$C_4$ alkylsulfonyl, $C_1$–$C_4$ alkanoylamino, $C_1$–$C_4$ alkylamino and N-($C_1$–$C_4$)alkyl-N-($C_1$–$C_4$)alkanoylamino, $Z^1$ is a group of the formula:

(wherein $R^3$ and $R^4$ are each independently a hydrogen atom, a $C_1$–$C_4$ alkyl group or an ar($C_1$–$C_4$)alkyl group or, when taken together with the adjacent nitrogen atom to which they are attached, represent a nitrogen-containing 5 to 7-membered saturated heterocyclic group optionally having an oxygen atom or an additional nitrogen atom as the hetero atom in addition to the said nitrogen atom and, in case of having the additional nitrogen atom, bearing a hydrogen atom, a $C_1$–$C_4$ alkyl group, an ar($C_1$–$C_4$)alkyl group or a phenyl group thereon),

is a group of the formula:

or the formula:

$A^1$ is a $C_2$–$C_6$ alkylene group and $A^2$ is a $C_2$–$C_4$ alkylene group.

In the significances as defined above, the term "halogen" includes fluorine, chlorine, bromine and iodine; the term "ar($C_1$–$C_4$)alkyl" covers benzyl, phenylethyl, phenylisopropyl, etc.; and the term "aryl" means phenyl, pyridyl, thienyl, furyl, naphthyl or the like. The terms "$C_1$–$C_4$ alkyl" and "$C_1$–$C_4$ alkoxy" each signify straight or branched chain alkyl and alkoxy groups having from 1 to 4 carbon atoms (e.g. methyl, ethyl, n-propyl, isopropyl, n-butyl, methxy, ethoxy, n-propoxy, isopropoxy, n-butyoxy, etc.), and the terms "$C_2$–$C_6$ alkylene" and "$C_2$–$C_4$ alkylene" mean straight or branched chain alkylene groups (e.g. ethylene, trimethylene, tetramethylene, pentamethylene, hexamethylene, methylethylene, methylpropylene, etc.). The term "heterocyclic" includes pyrrolidino, piperidino, homopiperidino, morpholino, piperazino, N-($C_1$–$C_4$)alkylpiperazino, N-ar($C_1$–$C_4$)alkylpiperazino, N-phenylpiperazino, etc.

In J.Pharmacol.Exptl.Therap., 112, 318-325 (1954), there are disclosed diphenylalkanoether derivatives of the general formula:

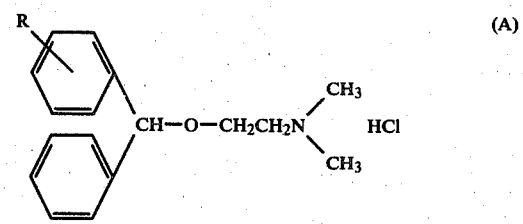

wherein R is a hydrogen atom, a halogen atom, an alkyl group or the like, which have antihistamine activity.

It has now unexpectedly been found that the diphenylalkanoether and diphenylalkanone oximeether derivatives (I) have various excellent pharmacological activities other than antihistamine activity. Particularly, these ethers (I) show cerebral and coronary vasodilating activity, antihypoxic activity, antispasmodic activity, inhibitory action of aggregation of blood platelets, etc. Moreover, the pharmacological actions of the ethers (I) are very strong; for instance, the cerebral vasodilating activity in rats is extremely greater than that of the compound (A). Therefore, the ethers (I) are therapeutically useful to treat cerebral or coronary arteriosclerosis, senile mental indolence and the results of cerebral insufficiency. From this point of view, preferred are those of the formula (I) wherein $R^1$ is phenyl or substituted phenyl, $R^2$ is phenyl and $A^1$ is trimethylene or tetramethylene. Particularly preferred are those of the formula (I) in which $R^1$ is phenyl or halophenyl, $R^2$ is phenyl, $A^1$ is trimethylene or tetramethylene and $Z^1$ is dimethylamino or piperidino.

Accordingly, a basic object of the present invention is to provide novel diphenylalkanoether and diphenylalkanone oximeether derivatives (I) having cerebral vasodilating activity, antihypoxic activity and the like. Another object of the invention is to provide a process for producing those ethers (I). These and other objects will be apparent to those skilled in the art to which the present invention pertains from the foregoing and subsequent descriptions.

According to the present invention, the ethers (I) can be prepared (a) by reacting a compound of the formula:

         (II)

wherein $R^6$ and $R^7$ are each independently an aryl group optionally substituted with 1 to 3 substituents selected from the group consisting of halogen, $C_1$–$C_4$ alkyl, $C_1$–$C_4$ alkoxy, nitro, cyano, di($C_1$–$C_4$)alkylamino, benzyloxy, $C_1$–$C_4$ alkylthio and N-($C_1$–$C_4$)alkyl-N-($C_1$–$C_4$)alkanoylamino,

is the formula:

or the formula:

and $A^1$ is as defined above with a halogen derivative of the formula:

$$D^1-A^2-Z^2 \quad \text{(III)}$$

wherein $D^1$ is a halogen atom, $Z^2$ is the same as defined with respect to the symbol $Z^1$ but excluding the cases where at least one of $R^3$ and $R^4$ is a hydrogen atom and where $Z^2$ is an unsubstituted piperazino group and $A^2$ is as defined above and optionally subjecting the resulting product to reduction of the nitro group, debenzylation of the benzyloxy or benzylamino group, acylation or alkylation of the amino group, oxidation of the $C_1$–$C_4$ alkylthio group and/or demethylation of the N-($C_1$–$C_4$)alkyl-N-methylamino group, or (b) by reacting a compound of the formula:

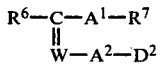 (IV)

wherein $D^2$ is a halogen atom, and $R^6$, $R^7$, $A^1$, $A^2$ and

are each as defined above with an amine of the formula:

$$H-Z^1 \quad \text{(V)}$$

wherein $Z^1$ is as defined above and optionally subjecting the resulting product to reduction of the nitro group, debenzylation of the benzyloxy or benzylamino group, acylation or alkylation of the amino group, oxidation of the $C_1$–$C_4$ alkylthio group and/or demethylation of the N-($C_1$–$C_4$)alkyl-N-methylamino group.

The diphenylalkanone oximeether derivatives of the formula:

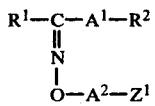 (VI)

wherein $R^1$, $R^2$, $A^1$, $A^2$ and $Z^1$ are each as defined above can be also prepared by reacting a ketone derivative of the formula:

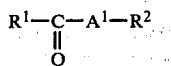 (VII)

wherein $R^1$, $R^2$ and $A^1$ are each as defined above with a hydroxylamine derivative of the formula:

$$H_2N-O-A^2-Z^1 \quad \text{(VIII)}$$

wherein $A^2$ and $Z^1$ are each as defined above and optionally subjecting the resultant product to reduction of the nitro group, debenzylation of the benzyloxy or benzylamino group, acylation or alkylation of the amino group, oxidation of the $C_1$–$C_4$ alkylthio group and/or demethylation of the N-($C_1$–$C_4$)alkyl-N-methylamino group.

The preparation process as above stated will be illustrated below in detail.

1. Production of the compound (I) from the compounds (II) and (III):

The compound (II) is reacted with the compound (III), usually in the presence of an alkali (e.g. alkali metal hydride, alkali metal alkoxide, alkali metal amide, alkali metal) in an inert solvent (e.g. benzene, toluene, xylene, dimethylformamide, dimethylsulfoxide) at a temperature ranging from 30° C. to the refluxing temperature of the reaction system (preferably from 50° to 150° C.) to give the compound (I).

2. Production of the compound (I) from the compounds (IV) and (V):

The compound (IV) is reacted with the compound (V), usually in an inert solvent at a temperature ranging from 0° C. to the refluxing temperature to give the compound (I). Examples of the inert solvent include alcohols (e.g. methanol, ethanol), ethers (e.g. tetrahydrofuran, dioxane), amides (e.g. dimethylformamide, dimethylacetamide), aromatic hydrocarbons (e.g. benzene, toluene, xylene), ketones (e.g. methylethylketone, methylisobutylketone) and dimethylsulfoxide. The reaction is preferably conducted in the presence of an alkali (e.g. alkali hydroxide, alkali carbonate, alkali hydrogen carbonate, triethylamine, pyridine).

3. Production of the compound (VI) from the compounds (VII) and (VIII):

The compound (VII) is reacted with the compound (VIII), usually in an inert solvent in the presence of an alkali (e.g. alkali hydroxide, alkali carbonate, alkali hydrogen carbonate, triethylamine, pyridine) at a temperature ranging from 20° C. to the refluxing temperature of the reaction system to give the compound (VI). Examples of the inert solvent are alkanol (e.g. methanol, ethanol, isopropanol), aqueous alkanol, dimethylformamide, dimethylsulfoxide, etc.

4. Reduction of the nitro group and debenzylation of the benzyloxy or benzylamino group:

These reactions may be accomplished by a per se conventional reduction procedure such as catalytic hydrogenation using palladium on charcoal as the catalyst. Debenzylation of the benzyloxy group can be also conducted by treatment with an acid (e.g. acetic acid, hydrochloric acid, Lewis acid).

5. Demethylation of the N-($C_1$–$C_4$)alkyl-N-methylamino group:

This reaction may be accomplished by a per se conventional procedure, preferably by treatment with ethyl chloroformate, followed by hydrolysis with an alkali.

6. Acylation of the amino group:

Acylation of the amino group may be accomplished by a per se conventional procedure, preferably by treatment with the corresponding acid halide (e.g. acetyl chloride, propionyl chloride, butyryl chloride) in the presence of an alkali at a temperature ranging from 0° to 30° C.

7. Alkylation of the amino group:

Alkylation of the amino group may be accomplished by a per se conventional procedure, for example, by treatment with the corresponding alkyl halide (e.g. methyl bromide, ethyl bromide) in the presence of an alkali at a temperature ranging from 20° C. to the refluxing temperature of the reaction system.

8. Oxidation of the $C_1$-$C_4$ alkylthio group:

Oxidation of the $C_1$-$C_4$ alkylthio group can be conducted by treatment with hydrogen peroxide or a peracid in an inert solvent at a temperature ranging from 20° to 50° C.

The starting materials (II) and (IV) of this invention may be prepared by the following procedures:

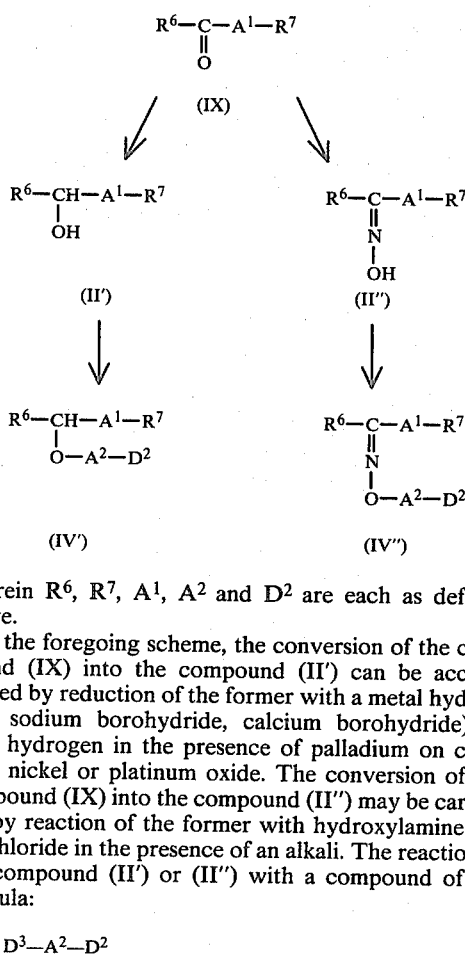

wherein $R^6$, $R^7$, $A^1$, $A^2$ and $D^2$ are each as defined above.

In the foregoing scheme, the conversion of the compound (IX) into the compound (II') can be accomplished by reduction of the former with a metal hydride (e.g. sodium borohydride, calcium borohydride) or with hydrogen in the presence of palladium on charcoal, nickel or platinum oxide. The conversion of the compound (IX) into the compound (II") may be carried out by reaction of the former with hydroxylamine hydrochloride in the presence of an alkali. The reaction of the compound (II') or (II") with a compound of the formula:

$$D^3-A^2-D^2 \qquad (X)$$

wherein $D^3$ is a halogen atom and $A^2$ and $D^2$ are each as defined above affords the compound (IV') or (IV"). The reaction may be effected in an inert solvent (e.g. benzene, tolene, xylene, dimethylformamide, dimethylsulfoxide) in the presence of an alkali at a temperature ranging from 30° C. to the refluxing temperature of the reaction system (preferably from 50° to 150° C.). Examples of the alkali are alkali metal, alkali metal alkoxide, alkali metal amide, alkali metal hydride, etc.

Specific examples of the diphenylalkanoether and diphenylalkanone oximeether derivatives (I) are as follows:

O-[3-(N,N-Dimethylamino)propyl]-1,4-diphenyl-1-butanone oxime;
O-[2-(N,N-Dimethylamino)ethyl]-1,4-diphenyl-1-butanone oxime;
O-[3-(4-Phenylpiperazino)propyl]-1,4-diphenyl-1-butanone oxime;
O-[3-(N,N-Dimethylamino)propyl]-1-(p-fluorophenyl)-4-phenyl-1-butanone oxime;
O-[3-(N,N-Dimethylamino)propyl]-1,3-diphenyl-1-propanone oxime;
O-[2-(N,N-Diethylamino)ethyl]-1,4-diphenyl-1-butanone oxime;
O-(3-Hexamethyleneiminopropyl)-1,4-diphenyl-1-butanone oxime;
O-(3-Piperidinopropyl)-1,4-diphenyl-1-butanone oxime;
O-[3-(N,N-Dimethylamino)propyl]-1,4-bis(3,4-dimethylphenyl)-1-butanone oxime;
O-[3-(N,N-Dimethylamino)propyl]-1-(3,4-dichlorophenyl)-4-phenyl-1-butanone oxime;
O-[4-(N,N-Dimethylamino)butyl]-1,4-bis(o-chlorophenyl)-1-butanone oxime;
O-[3-(N,N-Dimethylamino)propyl]-1-(p-methoxyphenyl)-5-phenyl-1-pentanone oxime;
O-[3-(N,N-Dimethylamino)propyl]-1-(m-methylphenyl)-6-phenyl-1-hexanone oxime;
O-[3-(N,N-Dimethylamino)propyl]-1-(2-pyridinyl)-4-phenyl-1-butanone oxime;
O-[3-(N,N-Dimethylamino)propyl]-1,4-bis-thienyl-1-butanone oxime;
O-[3-(N,N-Dimethylamino)propyl]-1-(p-dimethylaminophenyl)-4-phenyl-1-butanone oxime;
O-[3-(N,N-Dimethylamino)propyl]-1-(p-hydroxyphenyl)-4-phenyl-1-butanone oxime;
1-[3-(N,N-Dimethylamino)propoxy]-1,4-diphenylbutane;
1-[3-(N,N-Dimethylamino)propoxy]-1-(p-hydroxyphenyl)-4-phenylbutane;
1-[3-(N,N-Dimethylamino)propoxy]-1-(p-benzyloxyphenyl)-4-phenylbutane;
1-(3-Piperidinopropoxy)-1,4-diphenylbutane;
1-[3-(N,N-Dimethylamino)propoxy]-1,5-diphenylpentane;
1-(3-Piperidinopropoxy)-1,5-diphenylpentane;
1-[3-(N,N-Dimethylamino)propoxy]-1-(p-fluorophenyl)-4-phenylbutane;
1-[3-(N,N-Dimethylamino)propoxy]-1-(o-chlorophenyl)-4-phenylbutane;
1-[3-(N,N-Dimethylamino)propoxy]-1-(p-methoxyphenyl)-4-phenylbutane;
1-[2-(N,N-Diethylamino)ethoxy]-1,5-diphenylpentane;
1-[2-(N,N-Diethylamino)ethoxy]-1,4-diphenylbutane;
1-[3-(N,N-Dimethylamino)propoxy]-1-(p-dimethylaminophenyl)-4-phenylbutane;
1-[3-(N,N-Dimethylamino)propoxy]-1-thienyl-4-phenylbutane;
1-[3-(N,N-Dimethylamino)propoxy]-1-(2-pyridinyl)-4-phenylbutane;
1-[3-(N,N-Dimethylamino)propoxy]-1-(p-isopropylsulfinylphenyl)-4-phenylbutane;

1-[3-(N,N-Dimethylamino)propoxy]-1-(4-pyridinyl)-4-phenylbutane;
1-[3-(N,N-Dimethylamino)propoxy]-1-(p-methylphenyl)-4-phenylbutane;
1-[3-(N,N-Dimethylamino)propoxy]-1-(m,p-dimethoxyphenyl)-4-phenylbutane;
1-[3-(N,N-Dimethylamino)propoxy]-1,3-diphenylpropane;
1-[3-(N,N-Dimethylamino)propoxy]-1-furyl-4-phenylbutane;
1-(3-Morpholinopropoxy)-1,4-diphenylbutane;
1-[3-(4-Phenylpiperazino)propoxy]-1,4-diphenylbutane;
1-(3-Benzylaminopropoxy)-1,4-diphenylbutane;
1-[3-(4-Methylpiperazino)propoxy]-1,4-diphenylbutane;
1-[3-(N,N-Dimethylamino)propoxy]-1-(p-isopropylsulfonylphenyl)-4-phenylbutane;
1-[3-(4-Benzylpiperazino)propoxy]-1,4-diphenylbutane;
1-[2-(N,N-Dimethylamino)ethoxy]-1,3-diphenylpropane;
1-(3-Aminopropoxy)-1,4-diphenylbutane;
1-[3-(N-Methylamino)propoxy]-1,4-diphenylbutane;
1-[2-(N,N-Dimethylamino)ethoxy]-1,5-diphenylpentane;
1-[2-(N,N-Dimethylamino)ethoxy]-1,4-diphenylbutane;
1-[4-(N,N-Dimethylamino)butoxy]-1,4-diphenylbutane;
1-[3-(N,N-Dimethylamino)propoxy]-1,6-diphenylhexane;
1-[3-(N,N-Dimethylamino)propoxy]-1,7-diphenylheptane;
1-[3-(N-Methylamino)propoxy]-1-(p-fluorophenyl)-4-phenylbutane;
1-[3-(N,N-Dimethylamino)propoxy]-1-(p-cyanophenyl)-4-phenylbutane;
1-[3-(N,N-Dimethylamino)propoxy]-1-(p-nitrophenyl)-4-phenylbutane;
1-[3-(N,N-Dimethylamino)propoxy]-1-(p-aminophenyl)-4-phenylbutane;
1-[3-(N,N-Dimethylamino)propoxy]-1-(p-isopropylthiophenyl)-4-phenylbutane;
O-[3-(N,N-Dimethylamino)propyl]-1-(p-isopropylthiophenyl)-4-phenyl-1-butanone oxime;
O-[3-(N,N-Dimethylamino)propyl]-1-(p-acetaminophenyl)-4-phenyl-1-butanone oxime;
1-[3-(N,N-Dimethylamino)propoxy]-1-(p-methylaminophenyl)-4-phenylbutane.

The thus prepared diphenylalkanoether and diphenylalkanone oximeether derivatives (I) can be readily converted into their inorganic or organic acid addition salts by the conventional procedure.

For preparation of the pharmaceutical compositions, the ethers (I) or their salts may be mixed with carriers, diluents, lubricants, fillers and/or binders such as lactose, sucrose, calcium phosphate, starch, talcum, casein, magnesium stearate, methyl cellulose, polyglycols and tragacanth, sometimes together with stabilizers and emulsifying agents. The resulting mixture may be processed in a usual manner to tablets, capsules, pills, ampoules and the like. The usual oral dosage of the active ingredient is from about 10 to 200 mg daily.

Practical and presently preferred embodiments of the invention are illustratively shown in the following Examples without limiting the scope of the invention in any way.

EXAMPLE 1

A mixture of 3.0 g of 1,4-diphenyl-1-butanone oxime, 5.0 g of γ-dimethylaminopropyl chloride, 1.5 g of sodium hydride (65%) and 30 ml of toluene and heated under refluxing for 30 minutes. After cooling, the reaction mixture was poured into water and extracted with ethyl acetate. The organic layer was washed with water, dried over anhydrous sodium sulfate, concentrated under reduced pressure and chromatographed on silica gel to give O-[3-(N,N-Dimethylamino)propyl]-1,4-diphenyl-1-butanone oxime. M.P., 122°–124° C. (oxalate); 97°–98.5° C. (fumarate); 99°–100.5° C. (citrate).

EXAMPLE 2

In a similar manner to Example 1, the following compounds were prepared:

O-[2-(N,N-Dimethylamino)ethyl]-1,4-diphenyl-1-butanone oxime, M.P., 121.5°–123° C. (oxalate);
O-[3-(N,N-Dimethylamino)propyl]-1-(p-fluorophenyl)-4-phenyl-1-butanone oxime, M.P., 110°–111.5° C. (oxalate);
O-[3-(N,N-Dimethylamino)propyl]-1,3-diphenyl-1-propanone oxime, M.P., 123.5°–124° C. (oxalate);
O-[2-(N,N-Diethylamino)ethyl]-1,4-diphenyl-1-butanone oxime, M.P., 107°–108° C. (oxalate);
O-[3-(N,N-Dimethylamino)propyl]-1,5-diphenyl-1-pentanone oxime, M.P., 106°–111° C. (oxalate);
O-(3-Piperidinopropyl)-1,4-diphenyl-1-butanone oxime, M.P., 124°–125° C. (oxalate);
O-[3-(N,N-Dimethylamino)propyl]-1,4-bis(3,4-dimethylphenyl)-1-butanone oxime, M.P., 107°–108° C. (oxalate);
O-[3-(N,N-Dimethylamino)propyl]-1-(3,4-dichlorophenyl)-4-phenyl-1-butanone oxime, M.P., 106°–111° C. (oxalate), etc.

EXAMPLE 3

A mixture of 3.0 g of O-(3-chloropropyl)-1,4-diphenyl-1-butanone oxime, 10 ml of N-phenylpiperazine, 3 g of potassium carbonate and 30 ml of dimethylformamide was heated at 100° C. for 1 hour. After cooling, the reaction mixture was poured into water and extracted with ethyl acetate. The organic layer was washed with water, dried over anhydrous sodium sulfate, concentrated under reduced pressure and chromatographed on silica gel to give O-[3-(4-phenylpiperazino)propyl]-1,4-diphenyl-1-butanone oxime. M.P., 153°–155° C. (oxalate).

EXAMPLE 4

In a similar manner to Example 3, the following compounds were prepared:

O-(3-Hexamethyleneiminopropyl)-1,4-diphenyl-1-butanone oxime, M.P., 110°–111° C. (oxalate), etc.

EXAMPLE 5

A mixture of 5.0 g of 1-(p-fluorophenyl)-4-phenyl-1-butanol, 10 g of γ-dimethylaminopropyl chloride, 2.0 g of sodium hydride (65%) and 100 ml of toluene was heated under refluxing for 30 minutes. After cooling, the reaction mixture was poured into water and extracted with ethyl acetate. The organic layer was washed with water, dried over anhydrous sodium sulfate, concentrated under reduced pressure and chromatographed on silica gel to give 1-[3-(N,N-dimethylamino)propoxy]-1-(p-fluorophenyl)-4-phenylbutane. M.P., 80°–83° C. (fumarate).

EXAMPLE 6

In a similar manner to Example 5, the following compounds were prepared:

1-[3-(N,N-Dimethylamino)propoxy]-1-thienyl-4-phenylbutane, M.P., 70°–75° C. (fumarate);

1-[3-(N,N-Dimethylamino)propoxy]-1-(p-benzyloxyphenyl)-4-phenylbutane, reddish oil;

1-[3-(N,N-Dimethylamino)propoxy]-1,4-diphenylbutane, M.P., 105°–107° C. (oxalate), 89°–92° C. (citrate);

1-[3-(N,N-Dimethylamino)propoxy]-1,5-diphenylpentane, M.P., 81°–85° C. (oxalate);

1-[3-(N,N-Dimethylamino)propoxy]-1-(p-methoxyphenyl)-4-phenylbutane, M.P., 70°–73° C. (fumarate);

1-[3-(N,N-Dimethylamino)propoxy]-1-(4-pyridinyl)-4-phenylbutane, M.P., 103°–106° C. (fumarate);

1-[3-(N,N-Dimethylamino)propoxy]-1-(2-pyridinyl)-4-phenylbutane, M.P., 92°–94° C. (oxalate);

1-[3-(N,N-Dimethylamino)propoxy]-1-(p-dimethylaminophenyl)-4-phenylbutane, M.P., 77°–80° C. (fumarate);

1-[3-(N,N-Dimethylamino)propoxy]-1-(p-methylphenyl)-4-phenylbutane, M.P., 98°–102° C. (fumarate);

1-[3-(N,N-Dimethylamino)propoxy]-1-(m,p-dimethoxyphenyl)-4-phenylbutane, M.P., 79°–85° C. (oxalate);

1-[3-(N,N-Dimethylamino)propoxy]-1,3-diphenylpropane, M.P., 103°–105° C. (fumarate);

1-[3-(N,N-Dimethylamino)propoxy]-1-furyl-4-phenylbutane, M.P., 75°–85° C. (oxalate);

1-[3-(N,N-Dimethylamino)propoxy]-1-(o-chlorophenyl)-4-phenylbutane, M.P., 65°–70° C. (fumarate);

1-[3-(Piperidinopropoxy)-1,5-diphenylpentane, M.P., 112°–118° C. (oxalate);

1-(3-Piperidinopropoxy)-1,4-diphenylbutane, M.P., 81°–84° C. (fumarate);

1-[2-(N,N-Diethylamino)ethoxy]-1,5-diphenylpentane, M.P., 109°–112° C. (oxalate);

1-[2-(N,N-Dimethylamino)ethoxy]-1,4-diphenylbutane, M.P., 80°–81.5° C. (oxalate);

1-[2-(N,N-Dimethylamino)ethoxy]-1,3-diphenylpropane, M.P., 125°–126° C. (oxalate);

1-[3-(N,N-Dimethylamino)propoxy]-1-[p-(isopropylthio)phenyl]-4-phenylbutane, M.P., 96°–97° C. (fumarate);

1-[4-(N,N-Dimethylamino)butoxy]-1,4-diphenylbutane, M.P., 98°–99° C. (oxalate), etc.

EXAMPLE 7

A mixture of 1.5 g of 1-[3-(N,N-dimethylamino)propoxy]-1-(p-benzyloxyphenyl)-4-phenylbutane obtained in Example 6, 0.5 g of 10% palladium on charcoal (50% wet reagent), 1 g of acetic acid and 50 ml of ethanol was vigorously stirred in hydrogen atmosphere at room temperature until the theoretical amount of hydrogen was consumed. The reaction mixture was poured into water, made alkaline with aqueous ammonium hydroxide and extracted. After the catalyst was filtered off, the organic layer was washed with water, dried over anhydrous sodium sulfate and concentrated under reduced pressure to give 1-[3-(N,N-dimethylamino)propoxy]-1-(p-hydroxyphenyl)-4-phenylbutane. M.P., 91.5°–94.5° C. (oxalate).

EXAMPLE 8

A mixture of 1.5 g of 1-(3-chloropropoxy)-1,4-diphenylbutane, 7 ml of morpholine, 1.5 g of potassium carbonate and 15 ml of dimethylformamide was heated at 100° C. for 1 hour. After cooling, the reaction mixture was poured into water and extracted with ethyl acetate. The organic layer was washed with water, dried over anhydrous sodium sulfate, concentrated under reduced pressure and chromatographed on silica gel to give 1-(3-morpholinopropoxy)-1,4-diphenylbutane. M.P., 138°–139° C. (oxalate).

The starting 1-(3-chloropropoxy)-1,4-diphenylbutane was prepared as follows:

A mixture of 30 g of 1,4-diphenyl-1-butanol, 42 g of 1-bromo-3-chloropropane, 9.5 g of sodium hydride (65%) and 400 ml of toluene was heated under refluxing for 2 hours. After cooling, the reaction mixture was poured into water and extracted with ethyl acetate. The organic layer was washed with water, dried over anhydrous sodium sulfate and concentrated under reduced pressure to give 1-(3-chloropropoxy)-1,4-diphenylbutane.

EXAMPLE 9

In a similar manner to Example 8, the following compounds were prepared:

1-[3-(4-Methylpiperazino)propoxy]-1,4-diphenylbutane, M.P., 219°–221° C. (oxalate);

1-[3-(4-Phenylpiperazino)propoxy]-1,4-diphenylbutane, reddish oil, NMR δ (CDCl$_3$) (ppm), 3.32 (t), 4.20 (t);

1-[3-(Benzylamino)propoxy]-1,4-diphenylbutane, M.P., 97°–98° C. (oxalate);

1-[3-(Methylamino)propoxy]-1,4-diphenylbutane, M.P., 138°–140° C. (oxalate);

1-[3-(Isopropylamino)propoxy]-1,4-diphenylbutane, M.P., 107°–108° C. (oxalate);

1-(3-Aminopropoxy)-1,4-diphenylbutane, M.P., 143°–147° C. (oxalate), etc.

EXAMPLE 10

(a) A mixture of 1.0 g of 1-[3-(N,N-dimethylamino)propoxy]-1-(p-fluorophenyl)-4-phenylbutane, 2.75 g of potassium carbonate, 11 ml of ethyl chloroformate and 20 ml of toluene was heated under refluxing for 2 hours. After cooling, the reaction mixture was poured into water and extracted with ethyl acetate. The organic layer was washed with water, dried over anhydrous sodium sulfate and concentrated under reduced pressure to give 1-[3-(N-methyl-N-ethoxycarbonylamino)propoxy]-1-(p-fluorophenyl)-4-phenylbutane.

(b) A mixture of 0.9 g of 1-[3-(N-methyl-N-ethoxycarbonylamino)propoxy]-1-(p-fluorophenyl)-4-phenylbutane obtained above, 0.9 g of sodium hydroxide and 10 ml of dimethylsulfoxide was heated at 110° C. for 1 hour. After cooling, the reaction mixture was poured into water and extracted with ethyl acetate. The organic layer was washed with water, dried over anhydrous sodium sulfate and concentrated under reduced pressure to give 1-[3-(N-methylamino)propoxy]-1-(p-fluorophenyl)-4-phenylbutane, reddish oil, NMR δ (CDCl$_3$) (ppm), 2.43 (s), 3.30 (t), 4.01 (t).

What is claimed is:

1. A compound of the formula:

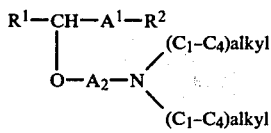

wherein $R^1$ and $R^2$ are each independently a phenyl, thienyl, furyl or naphthyl group optionally substituted with 1 to 3 substituents selected from the group consisting of halogen, $C_1$-$C_4$ alkyl, $C_1$-$C_4$ alkoxy, nitro, cyano, di($C_1$-$C_4$)alkylamino, amino, benzyloxy, hydroxyl, $C_1$-$C_4$ alkylthio, $C_1$-$C_4$ alkylsulfinyl, $C_1$-$C_4$ alkylsulfonyl, $C_1$-$C_4$ alkanoylamino, $C_1$-$C_4$ alkylamino and N-($C_1$-$C_4$)alkyl-N-($C_1$-$C_4$)alkanoylamino, $A^1$ is a $C_3$-$C_6$ alkylene group and $A^2$ is a $C_2$-$C_4$ alkylene group.

2. The compound according to claim 1, wherein $R^1$ is a phenyl group optionally substituted with 1 or 2 substituents selected from the group consisting of halogen, $C_1$-$C_4$ alkyl, $C_1$-$C_4$ alkoxy, di($C_1$-$C_4$)alkylamino, benzyloxy hydroxyl and $C_1$-$C_4$ alkylthio.

3. The compound according to claim 1, wherein $R^2$ is a phenyl group optionally substituted with $C_1$-$C_4$ alkyl or halogen.

4. The compound according to claim 1, wherein $R^2$ is a phenyl group.

5. A compound of the formula:

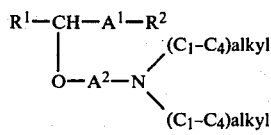

wherein $R^1$ is a phenyl group or a halophenyl group, $R^2$ is a phenyl group, $A^1$ is a $C_3$-$C_6$ alkylene group and $A^2$ is a $C_2$-$C_4$ alkylene group.

6. A compound of the formula:

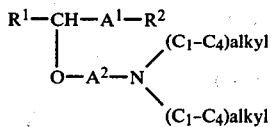

wherein $R^1$ and $R^2$ are each independently a phenyl group optionally substituted with 1 to 3 substituents selected from the group consisting of halogen, $C_1$-$C_4$ alkyl, $C_1$-$C_4$ alkoxy, nitro, cyano, di($C_1$-$C_4$)alkylamino, amino, benzyloxy, hydroxyl, $C_1$-$C_4$ alkylthio, $C_1$-$C_4$ alkylsulfinyl, $C_1$-$C_4$ alkylsulfonyl, $C_1$-$C_4$ alkanoylamino, $C_1$-$C_4$ alkylamino and N-($C_1$-$C_4$)alkyl-N-($C_1$-$C_4$)alkanoylamino, $A^1$ is a $C_3$-$C_6$ alkylene group and $A^2$ is a $C_2$-$C_4$ alkylene group.

7. A compound of the formula:

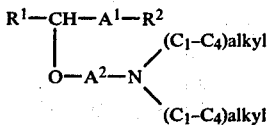

wherein $R^1$ is a phenyl group or a halophenyl group and $R^2$ is a phenyl group, $A^1$ is a $C_3$-$C_4$ alkylene group and $A^2$ is a $C_2$-$C_4$ alkylene group.

8. A compound of the formula:

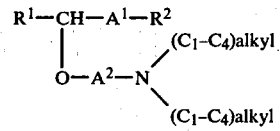

wherein $R^1$ and $R^2$ are each independently a phenyl group optionally substituted with 1 to 3 substituents selected from the group consisting of halogen, $C_1$-$C_4$ alkyl, $C_1$-$C_4$ alkoxy, nitro, cyano, di($C_1$-$C_4$)alkylamino, amino, benzyloxy, hydroxyl, $C_1$-$C_4$ alkylthio, $C_1$-$C_4$ alkylsulfinyl, $C_1$-$C_4$ alkylsulfonyl, $C_1$-$C_4$ alkanoylamino, $C_1$-$C_4$ alkylamino and N-($C_1$-$C_4$)alkyl-N-($C_1$-$C_4$) alkanoylamino, $A^1$ is a $C_3$-$C_4$ alkylene group and $A^2$ is a $C_2$-$C_4$ alkylene group.

9. A compound of the formula:

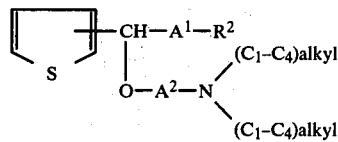

wherein $R^2$ is a phenyl, thienyl, furyl or naphthyl group optionally substituted with 1 to 3 substituents selected from the group consisting of halogen, $C_1$-$C_4$ alkyl, $C_1$-$C_4$ alkoxy, nitro, cyano, di($C_1$-$C_4$)alkylamino, amino, benzyloxy, hydroxyl, $C_1$-$C_4$ alkylthio, $C_1$-$C_4$ alkylsulfinyl, $C_1$-$C_4$ alkylsulfonyl, $C_1$-$C_4$ alkanoylamino, $C_1$-$C_4$ alkylamino and N-($C_1$-$C_4$)alkyl-N-($C_1$-$C_4$)alkanoylamino, $A^1$ is a $C_2$-$C_6$ alkylene group and $A^2$ is a $C_2$-$C_4$ alkylene group.

10. A compound of the formula:

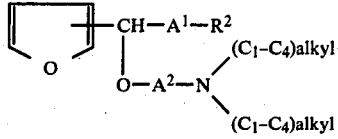

wherein $R^2$ is a phenyl, thienyl, furyl or naphthyl group optionally substituted with 1 to 3 substituents selected from the group consisting of halogen, $C_1$-$C_4$ alkyl, $C_1$-$C_4$ alkoxy, nitro, cyano, di($C_1$-$C_4$)alkylamino, amino, benzyloxy, hydroxyl, $C_1$-$C_4$ alkylthio, $C_1$-$C_4$ alkylsulfinyl, $C_1$-$C_4$ alkylsulfonyl, $C_1$-$C_4$ alkanoylamino, $C_1$-$C_4$ alkylamino and N-($C_1$-$C_4$)alkyl-N-($C_1$-$C_4$)alkanoylamino, $A^1$ is a $C_2$-$C_6$ alkylene group and $A^2$ is a $C_2$-$C_4$ alkylene group.

11. 1-[3-(N,N-Dimethylamino)propoxy]-1,4-diphenylbutane, or a non-toxic, pharmaceutically acceptable acid addition salt thereof.

12. 1-[3-(N,N-Dimethylamino)propoxy]-1-(p-fluorophenyl)-4-phenylbutane, or a non-toxic, pharmaceutically acceptable acid addition salt thereof.

13. 1-[3-(N,N-Dimethylamino)propoxy]-1,5-diphenylpentane, or a non-toxic, pharmaceutically acceptable acid addition salt thereof.

14. 1-[3-(N,N-Dimethylamino)propoxy]-1-thienyl-4-phenylbutane, or a non-toxic, pharmaceutically acceptable acid addition salt thereof.

15. 1-[3-(N,N-Dimethylamino)propoxy]-1-furyl-4-phenylbutane, or a non-toxic, pharmaceutically acceptable acid addition salt thereof.

* * * * *

UNITED STATES PATENT AND TRADEMARK OFFICE
CERTIFICATE OF CORRECTION

PATENT NO. : 4,388,469
DATED : June 14, 1983
INVENTOR(S) : Keiichi ONO et al

It is certified that error appears in the above—identified patent and that said Letters Patent are hereby corrected as shown below:

In Column 12, line 33, change "$C_2$-$C_6$" to --$C_3$-$C_6$--;

line 51, change "$C_2$-$C_6$" to --$C_3$-$C_6$--.

Signed and Sealed this

Thirty-first Day of July 1984

[SEAL]

Attest:

GERALD J. MOSSINGHOFF

Attesting Officer — Commissioner of Patents and Trademarks